United States Patent
Hayashi et al.

(10) Patent No.: US 7,056,862 B2
(45) Date of Patent: Jun. 6, 2006

(54) HERBICIDE POTENTIATORS

(75) Inventors: Toshio Hayashi, Wakayama (JP); Tadayuki Suzuki, Wakayama (JP); Kazuhiko Kurita, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/432,927

(22) PCT Filed: Dec. 19, 2001

(86) PCT No.: PCT/JP01/11142

§ 371 (c)(1),
(2), (4) Date: Oct. 27, 2003

(87) PCT Pub. No.: WO02/49429

PCT Pub. Date: Jun. 27, 2002

(65) Prior Publication Data

US 2004/0053788 A1    Mar. 18, 2004

(30) Foreign Application Priority Data

Dec. 20, 2000    (JP) .................. 2000-386954

(51) Int. Cl.
*A01N 25/30* (2006.01)

(52) U.S. Cl. ............ 504/116.1; 504/313; 504/314; 504/318; 504/351; 504/352; 504/353; 514/529; 514/546; 514/715; 514/717; 514/718; 514/720; 514/721; 514/724

(58) Field of Classification Search ........... 504/116.1, 504/313, 314, 318, 351–353; 514/529, 546, 514/715, 717, 718, 720, 721, 724
See application file for complete search history.

(56) References Cited

U.S. PATENT DOCUMENTS

| 4,084,956 | A | * | 4/1978 | Doyle et al. ............ 504/304 |
| 4,626,274 | A |   | 12/1986 | Hausmann et al. |
| 5,385,750 | A |   | 1/1995 | Aleksejczyk et al. |
| 5,622,911 | A |   | 4/1997 | Hasebe et al. |
| 6,489,269 | B1 | * | 12/2002 | Hayashi et al. ......... 504/353 |

FOREIGN PATENT DOCUMENTS

| EP | 0 968 649 | * | 1/2000 |
| JP | 49-93542 |   | 9/1974 |
| JP | 57-24303 A |   | 2/1982 |
| JP | 62-56401 A |   | 3/1987 |
| JP | 62-240602 A |   | 10/1987 |
| JP | 7-508024 A |   | 9/1995 |
| JP | 9-143016 | * | 6/1997 |
| JP | 2000-198703 A | * | 7/2000 |
| WO | WO 93/22917 A1 |   | 11/1993 |
| WO | 96/31121 | * | 10/1996 |

OTHER PUBLICATIONS

The Merck Index. 11$^{th}$ ed. Merck & Co. Entries 3402, 4393,75327554, 7555. 1989.*

* cited by examiner

*Primary Examiner*—S. Mark Clardy
(74) *Attorney, Agent, or Firm*—Birch, Stewart, Kolasch & Birch, LLP

(57) ABSTRACT

The invention provides an agricultural chemical enhancer and an agricultural chemical composition which are safely used for crops without any phytotoxicity, have a potency enhancing action on various agricultural chemicals and promote the growth of a plant body to be intended to be grown. The invention relates to an agricultural chemical enhancer comprising at least one type selected from a specific alcohol compound, an ether compound and an ester compound.

8 Claims, No Drawings

HERBICIDE POTENTIATORS

This application is the national phase under 35 U.S.C. § 371 of PCT International Application No. PCT/JP01/11142 which has an International filing date of Dec. 19, 2001, which designated the United States of America.

TECHNICAL FIELD

The present invention relates to a novel agricultural chemical enhancer and a novel agricultural chemical composition.

BACKGROUND ART

Agricultural chemicals including insecticides, fungicides (or bactericides), herbicides, miticides and plant growth regulators are used in the formulations such as emulsifiable concentrates, wettable powders, granules, dust formulations and suspension concentrates (flowable). At this time, various ideas on the qualities of formulations are carried out to draw out the effect of a technical material of agricultural chemical. However, it is difficult at present to more enhance the effect of an agricultural chemical by devising formulations. Also, because it is more difficult to develop a new agricultural chemical, it is industrially significant to more enhance the activity of currently used agricultural chemicals.

U.S. Pat. No. 5,385,750 (corresponding to JP-A No. 7-508024 and WO93/22917) discloses a method of improving the wettability of an aqueous mixture by using an alkyl glycoside and a C7-20 aliphatic alcohol. However, there is no description as to more enhancement in the activity of a current agricultural chemical and the promotion of the growth of a target plant.

DISCLOSURE OF THE INVENTION

The present invention provides an agricultural chemical enhancer comprising at least one type among a compound represented by the formula (I), a compound represented by the formula (II) and a compound represented by the formula (III) as an effective component.

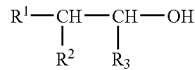  (I)

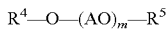  (II)

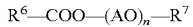  (III)

wherein $R^1$ represents a hydrocarbon group having 10 to 22 carbon atoms, $R^2$ represents a hydrogen atom, a hydroxyl group or a hydrocarbon group having 1 to 24 carbon atoms, $R^3$ represents a hydrogen atom or a hydrocarbon group having 1 to 24 carbon atoms, $R^4$ represents a hydrocarbon group having 12 to 24 carbon atoms, $R^5$ represents a hydrocarbon group having 1 to 24 carbon atoms, AO represents an alkylene oxide group having 2 to 4 carbon atoms, m denotes a number of 0 to 50, n denotes a number of 0 to 50, $R^6$ represents a hydrocarbon group having 11 to 23 carbon atoms and $R^7$ represents a hydrocarbon group having 12 to 24 carbon atoms or $—COR^8$, where $R^8$ represents a hydrocarbon group having 11 to 23 carbon atoms.

Moreover, the present invention provides an agricultural chemical enhancer composition comprising a compound represented by the above formulae (I), (II) and (III) and at least one of a surfactant other than this compound and a chelating agent. The surfactant is preferably at least one of (1) a nonionic surfactant having at least one of an ester bond, an ether bond and an amide bond, (2) an anionic surfactant, (3) a cationic surfactant and (4) an amphoteric surfactant. Particularly, the surfactant is more preferably (1) a nonionic surfactant having at least one of an ester bond and an ether bond.

Also, the present invention provides an agricultural chemical composition comprising the aforementioned agricultural chemical enhancer or composition and a technical material of agricultural chemical. Further, the present invention also provides the use for enhancing the potency of an agricultural chemical and for improving the growth of a plant by using the aforementioned agricultural chemical enhancer or composition. The present invention also provides a method for enhancing the potency of an agricultural chemical and for improving the growth of a plant by applying the aforementioned agricultural chemical enhancer or composition to a plant together with an agricultural chemical.

DETAILED DESCRIPTION OF THE INVENTION

In the present invention, at least one of compounds represented by the aforementioned formulae (I) to (III) is used as an effective component in an agricultural chemical enhancer having the effect of more enhancing the activity of an agricultural chemical and of promoting the growth of a plant body to be intended to be grown. Among these compounds, the compound represented by the formula (I) and the compound represented by the formula (II) are preferable and the compound represented by the formula (I) is most preferable.

In the formulae (I) to (III), $R^1$, $R^2$, $R^3$, $R^4$, $R^5$, $R^6$, $R^7$ and $R^8$ may be saturated or unsaturated and is preferably saturated. Also, these hydrocarbon groups may be any of straight-chain, branched and cyclic types, are preferably a straight-chain or branched types and are particularly preferably straight-chain types.

Also, the total carbon number of $R^1$, $R^2$ and $R^3$, the total carbon number of $R^4$ and $R^5$ and the total carbon number of $R^6$, $R^7$ and $R^8$ are all preferably 50 or less, more preferably 12 to 48 and still more preferably 16 to 44.

In the formula (I), the carbon number of $R^1$ is preferably 14 to 22, more preferably 14 to 20 and still more preferably 14 to 18. Also, the total carbon number of the compound represented by the formula (I) is preferably 12 to 48, more preferably 16 to 28 and particularly preferably 16 to 24. Further, the compound represented by the formula (I) is preferably those having a total carbon number of 12 to 24 and one hydroxyl group and particularly preferably those having a total carbon number of 16 to 22 and one hydroxyl group. Specific examples of the compound represented by the formula (I) include the following compounds.

(I-1)

1-Alkanols represented by the formula $CH_3(CH_2)_{o-1}OH$ (o is an integer of 12 to 24, preferably 16 to 24 and more preferably 16 to 20) are exemplified. Specific examples include 1-dodecanol, 1-tridecanol, 1-tetradecanol, 1-pentadecanol, 1-hexadecanol, 1-heptadecanol, 1-octadecanol, 1-nonadecanol, 1-eicosanol, 1-heneicosanol, 1-docosanol, 1-tricosanol and 1-tetracosanol.

(I-2)

2-Alkanols represented by the formula $CH_3CH(OH)(CH_2)_{p-3}CH_3$ (p is an integer of 12 to 24, preferably 16 to 24 and more preferably 16 to 20) are exemplified. Specific examples include 2-dedecanol, 2-tridecanol, 2-tetradecanol, 2-pentadecanol, 2-hexadecanol, 2-heptadecanol, 2-octadecanol, 2-nonadecanol, 2-eicosanol, etc.

(I-3)

Terminal unsaturated alcohols represented by the formula $CH_2=CH(CH_2)_{q-2}OH$ (q is an integer of 12 to 24, preferably 16 to 24 and more preferably 16 to 20) are exemplified. Specific examples include 11-dodecene-1-ol, 12-tridecene-1-ol, 15-hexadecene-1-ol, etc.

(I-4)

Examples of other unsaturated alcohols include oleyl alcohol, elaidyl alcohol, linoleyl alcohol, linolenyl alcohol, eleostearyl alcohol (α or β), ricinoyl alcohol, etc.

(I-5)

1,2-Diols represented by $HOCH_2CH(OH)(CH_2)_{r-2}H$ (r is an integer of 12 to 24, preferably 16 to 24 and more preferably 16 to 20) are exemplified. Specific examples include 1,2-dodecanediol, 1,2-tetradecanediol, 1,2-hexadecanediol, 1,2-octadecanediol, etc.

Among the aforementioned (I-1) to (I-5), (I-1), (I-2), (I-4) and (I-5) are preferable, (I-1), (I-2) and (I-4) are more preferable, (I-1) and (I-4) are still more preferable and (I-1) is particularly preferable.

Also, the total carbon number of the compound represented by the formula (II) is preferably 13 to 48, more preferably 24 to 48 and particularly preferably 32 to 40. m in the formula (II) is preferably 0 to 30, more preferably 0 to 10 and particularly preferably 0 to 5. Specific examples of the compound represented by the formula (II) include following compounds.

(II-1)

Di-n-alkyl ethers represented by $CH_3(CH_2)_{s-1}-O-(CH_2)_{s-1}CH_3$ (s is an integer of 12 to 24, preferably 16 to 24 and more preferably 16 to 20) are exemplified. Specific examples include didodecyl ether, ditridecyl ether, ditetradecyl ether, dipentadecyl ether, dihexadecyl ether, dioctadecyl ether, etc.

(II-2)

Vinyl ethers represented by $CH_2=CH-OR^5$ ($R^5$ represents an alkyl group or an alkenyl group having 12 to 24 and preferably 16 to 24 carbon atoms) are exemplified. Specific examples include vinyl lauryl ether, vinyl myristyl ether, vinyl cetyl ether, vinyl stearyl ether, vinyl oleyl ether, vinyl linoleyl ether, etc.

Among the aforementioned (II-1) and (II-2), (II-1) is preferable.

Also, the total carbon number of the compound represented by the formula (III) is preferably 24 to 48, more preferably 28 to 48 and particularly preferably 32 to 44. n in the formula (III) is preferably 0 to 30, more preferably 0 to 10 and particularly preferably 0 to 5. $R^6$, $R^7$ and $R^8$ in the formula (III) are preferably straight-chain types or saturated types and particularly preferably straight-chain saturated types. The compound represented by the formula (III) has an HLB (according to the Griffin's equation) preferably less than 7, an HLB of more preferably 6 or less, still more preferably 5 or less and particularly preferably 4 or less. According to this Griffin's equation, HLB is expressed by the following formula: HLB=(molecular weight of hydrophilic part/molecular weight of surfactant)×(100/5) ("NEW PRIMER HANDBOOK OF SURFACTANT", Sanyo Chemical Industries, Ltd., published on Nov. 1, 1985, page 128). Specific examples of the compound represented by the formula (III) include the following compounds.

(III-1) Ethylene glycol fatty acid diesters represented by $R^{6\prime}-COO-CH_2CH_2OCOR^{8\prime}$ ($R^{6\prime}$ and $R^{8\prime}$, which may be the same or different, respectively represent an alkyl group or an alkenyl group having 11 to 23, preferably 15 to 23 and particularly preferably 15 to 19 carbon atoms are exemplified. Specific examples include ethylene glycol dilaurate, ethylene glycol dimyristate, ethylene glycol dipalmitate and ethylene glycol distearate.

(III-2) Fatty acid esters represented by $R^{6\prime}-COO-R^{7\prime}$ ($R^{6\prime}$ represents an alkyl group or an alkenyl group having 11 to 23, preferably 15 to 23 and particularly preferably 15 to 19 carbon atoms and $R^{7\prime}$ represents an alkyl group or an alkenyl group having 12 to 24, preferably 16 to 24 and particularly preferably 16 to 20 carbon atoms) are exemplified. Specific examples include lauryl palmitate, palmityl palmitate, stearyl palmitate, lauryl stearate, palmityl stearate, stearyl stearate, etc.

Among the aforementioned (III-1) and (III-2), (III-2) is preferable.

Although a mechanism as to whether or not the agricultural chemical enhancer of the present invention has a significant potency enhancing action irrespective of the type of structure of an agricultural chemical is not necessarily clear, it is inferred in one of the mechanism that because the enhancer of the present invention has very strong solubilizing ability in an agricultural chemical, it micronizes the agricultural chemical and therefore stimulates the permeability of the agricultural chemical into plant bodies, insect bodies and bacteria bodies. The formulation form of the agricultural chemical enhancer of the present invention may be any one of a liquid form, powder form, granular form, etc. though not limited to these forms.

As a method of using the agricultural chemical enhancer according to the present invention, there are a method of using an agricultural chemical composition containing the agricultural chemical enhancer and a method of using the agricultural chemical enhancer to be separately added when diluting and using an agricultural chemical (excluding the enhancer of the present invention) The potency enhancing ability to be intended in the present invention is obtained by any one of these methods. Also, the agricultural chemical enhancer according to the present invention can be used safely without giving any chemical injury to various crops.

In the agricultural chemical enhancer of the present invention, at least one of the compounds represented by the formulae (I) to (III) is used together with a surfactant other than these compounds, whereby the amount of the compounds represented by the formulae (I) to (III) can be reduced, maintaining the enhancing effect of the compounds represented by the formulae (I) to (III) on an agricultural chemical. The HLB (according to Griffin's equation) of the surfactant is preferably 7 or more, more preferably 8 or more, still more preferably 9 or more and particularly preferably 10 or more.

As the surfactant, at least one of (1) a nonionic surfactant having at least one of an ester bond, an ether bond or an amide bond, (2) an anionic surfactant, (3) a cationic surfactant and (4) an amphoteric surfactant is preferable.

Examples of the nonionic surfactant having at least one of an ester bond, an ether bond and an amide bond include a sorbitan fatty acid ester, polyoxyalkylene sorbitan fatty acid ester, sucrose fatty acid ester, sorbitol fatty acid ester, polyoxyalkylene sorbitol fatty acid ester, polyglycerol fatty acid ester, glycerol fatty acid ester and polyoxyalkylene glycerol fatty acid ester such as polyoxyethylene hardened castor oil, alkylene glycol fatty acid ester and polyalkylene glycol fatty acid ester as the ester type, a polyoxyalkylene alkyl ether such as POE (20) lauryl ether, polyoxyalkylene alkylaryl ether, alkyl glyceryl ether, polyglycerol and polyoxyalkylene block copolymer (Pluronic type) as the ether type and an alkylalkanolamide and saccharide type fatty acid amide as the amide type. Here, as the saccharide type amide, those having a structure in which a hydrophobic group is amide-bonded with a sugar or with a sugaralcohol are exemplified. Examples of the saccharide type fatty acid amide include saccharaide type fatty acid amides such as fatty acid amides of glucose or fructose. Also, those having a structure in which a hydrophobic group is amide-bonded with a sugar or with a sugar alcohol having an amino group, for example, saccharide type fatty acid amides such as a fatty acid amide of N-methyl glucamine may be used.

As the saccharide type fatty acid amide, compounds represented by the formula (1) may be preferably used.

$$R^{11}\text{—CO—NR}^{12}X \quad (1)$$

wherein $R^{11}$ represents a straight-chain or branched alkyl group or alkenyl group having 5 to 17 carbon atoms or an alkylphenyl group, $R^{12}$ represents hydrogen, a straight-chain or branched alkyl group or alkenyl group having 1 to 18 carbon atoms, —$(CH_2CH(R^{13})O)_c$—H (where $R^{13}$ represents hydrogen or a methyl group and c denotes a number from 0 to 10), —$CH_2CH_2OH$, —$CH_2CH(OH)CH_3$ or —$CH_2CH_2CH_2OH$ and X represents a polyhydroxyalkyl group consisting of a sugar residue having 4 to 30 carbon atoms.

Examples of $R^{11}$ in the formula (1) may include groups with $R^{11}CO$ derived from capric acid, caprylic acid, lauric acid, myristic acid, palmitic acid, stearic acid or isostearic acid among the straight-chain or branched alkyl or alkenyl groups or alkylphenyl groups and groups derived from capric acid or lauric acid may be particularly preferably exemplified.

Specific examples of $R^{12}$ preferably include hydrogen, a methyl group, ethyl group, n-propyl group, isopropyl group, n-butyl group, t-butyl group, n-hexyl group, octyl group, 2-ethylhexyl group, decyl group, dodecyl group, stearyl group, isostearyl group or polyethylene glycol group having a degree of polymerization of 2 to 10 or polypropylene glycol group, 2-hydroxyethyl group, 2-hydroxypropyl group, 3-hydroxypropyl group, etc. Among these groups, hydrogen, a methyl group, ethyl group, 2-hydroxyethyl group, 2-hydroxypropyl group and 3-hydroxypropyl group are preferably exemplified.

It is to be noted that the polyhydroxyalkyl groups consisting of a sugar residue having 4 to 30 carbon atoms as X include polyhydroxyalkyl groups which are glycoside-bonded with a mono-, di- or oligosaccharide group and have 4 to 7 carbon atoms.

The aforementioned nonionic surfactants may be used either singly or in the form of a mixture of two or more.

A typical one as the anionic surfactant (2) is available in the form of an aqueous solution or a solid. Examples of the anionic surfactant include a sodium mono- or di-alkylnaphthalenesulfonate, sodium α-olefinsulfonate, sodium alkanesulfonate, alkyl sulfosuccinate, alkyl sulfate, polyoxyalkylene alkyl ether sulfate, polyoxyalkylene alkylaryl ether sulfate, polyoxyalkylene styrylphenyl ether sulfate, mono- or di-alkylbenzene sulfonate, alkylnaphthalene sulfonate, formaldehyde condensate of an alkylnaphthalene sulfonate, alkyl diphenyl ether sulfonate, olefinic sulfonate, mono- or di-alkyl phosphate, polyoxyalkylene mono- or di-alkylphosphate, polyoxyalkylene mono- or di-phenyl ether phosphate, polyoxyalkylene mono- or di-alkylphenyl ether phosphate, polycarboxylate, a fatty acid salt, a straight-chain or branched alkyl polyoxyalkylene ether acetic acid or its salt, alkenyl polyoxyalkylene ether acetic acid or its salt, stearic acid and its salt, oleic acid and its salt, N-methyl fatty acid taurides and mixtures of two or more of these compounds (including sodium, potassium, ammonium or amine salts).

Examples of the cationic surfactant (3) include alkylamine ethylene oxide adducts and alkylamine propylene oxide adducts, for example, tallowamine ethylene oxide adducts, oleylamine ethylene oxide adducts, soyamine ethylene oxide adducts, cocoamine ethylene oxide adducts, synthetic alkylamine ethylene oxide adducts, octylamine ethylene oxide adducts, alkanolamine alkyl esterified products and their alkylene oxide adducts, quaternary ammonium compounds derived from these compounds and mixtures of these compounds as described in WO95/33379.

Examples of the amphoteric surfactant (4) include laurydimethylaminoacetic acid betaine, alkyldimethylamine oxide, alkylcarboxymethylhydroxyethylimidazoliumbetaine, alkylamidopropylbetaine and alkylhydroxysulfobetaine and mixtures of these compounds.

Among these surfactants, at least one of the aforementioned nonionic surfactants having a specific bond and anionic surfactants is preferable and the aforementioned nonionic surfactants having a specific bond are particularly preferable.

Among the aforementioned surfactants, ester types and ether types are preferable and particularly ester types are preferable. Among these ester types, sorbitan fatty acid esters such as POE (20) sorbitan monooleate, polyoxyalkylene sorbitan fatty acid esters and polyoxyethylene hardened castor oil such as POE (20) hardened castor oil are preferable.

In the agricultural chemical enhancer comprising, as essential components, the compounds represented by the formulae (I) to (III) and the surfactant other than these compounds, the ratio of the total amount of the compound represented by the formula (I) to the surfactant is as follows: [total amount of the compound represented by the formula (I)]/[surfactant other than these compounds]=preferably 0.01 to 100 (weight ratio), more preferably 0.05 to 50 and particularly preferably 0.1 to 10.

The agricultural chemical enhancer of the present invention may be compounded further with a chelating agent in at least one of the compounds represented by the formulae (I) to (III). The potency enhancing effect of an agricultural chemical can be more improved by compounding the chelating agent. Examples of the chelating agent include an aminopolycarboxylic acid type chelating agent, aromatic or aliphatic carboxylic acid type chelating agent, amino acid type chelating agent, ether polycarboxylic acid type chelating agent, phosphonic acid type chelating agent (e.g., iminodimethylphosphonic acid (IDP), alkyldiphosphonic acid (ADPA)) or dimethylglyoxime (DG), etc. These compounds may be acids as they are or in the form of, for example, a salt of sodium, potassium or ammonium. In the present invention, the chelating agent is compounded in an amount of preferably 0.001 to 30 mol equivalents, more preferably 0.01 to 20 mol equivalents and particularly preferably 0.05 to 15 mol equivalents to one mol of the compounds represented by the formulae (I) to (III).

As the aminopolycarboxylic acid type chelating agent, the following compounds may be all used:
a) $RNX_2$ type compounds;
b) $NX_3$ type compounds;

c) R-NX-CH$_2$CH$_2$-NX-R type compounds;
d) R-NX-CH$_2$CH$_2$-NX$_2$ type compounds; and
e) X$_2$N-R'-NX$_2$ type compounds wherein four or more Xs are included. In the above formula, X represents —CH$_2$COOH or —CH$_2$CH$_2$COOH, R represents a hydrogen atom, an alkyl group, a hydroxyl group, a hydroxyalkyl group or a substituent representing known chelating agents of this type and R' represents an alkylene group, a cycloalkylene group or a substituent representing known chelating agents of this type Typical examples of chelating agents include ethylenediamine tetraacetic acid (EDTA) such as EDTA·4Na, cyclohexanediamine tetraacetic acid (CDTA), nitrilotriacetic acid (NTA), iminodiacetic acid (IDA), N-(2-hydroxyethyl)iminodiacetic acid (HIMDA), diethylenetriamine pentaacetic acid (DTPA), N-(2-hydroxyethyl)ethylenediamine triacetic acid (EDTA-OH) and glycol ether diamine tetraacetic acid (GEDTA), salts of these compounds, etc.

Examples of the aromatic or aliphatic carboxylic acid type chelating agent include citric acid, gluconic acid, malic acid, heptonic acid, oxalic acid, malonic acid, lactic acid, tartaric acid, succinic acid, fumaric acid, maleic acid, adipic acid, oxycarboxylic acid such as glutaric acid, polyvalent carboxylic acid and potassium salts, sodium salts, alkanolamine salts and aliphatic amine salts of these acids.

Examples of the amino acid type chelating agent include glycine, cerin, alanine, lysine, cystine, cysteine, ethionine, tyrosine and methionine and salts or derivatives of these compounds. Further, examples of the ether polycarboxylic acid type chelating agent include compounds represented by the following formula, their analogous compounds and their salts (especially Na salts).

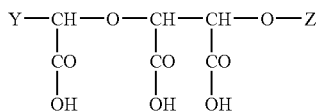

wherein Y represents a hydrogen atom, a group represented by the formula: —CH$_2$COOH or a group represented by the formula: —COOH, Z represents a hydrogen atom, a group represented by the formula: —CH$_2$COOH or a group represented by the formula:

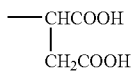

A solvent and a permeability adjuvant may be used together in the agricultural chemical enhancer of the present invention. Examples of the solvent or the permeability adjuvant are as follows.

1) Water including ion exchange water, aqueous organic or inorganic solutions and aqueous alkali solutions.
2) Monohydric alcohols having 1 to 11 carbon atoms such as ethanol, n-hexanol, 2-heptanol, n-octanol, 2-ethylhexanol, n-decanol, cyclohexanol and benzyl alcohol.
3) Polyhydric alcohols having 2 to 11 carbon atoms such as ethylene glycol, propylene glycol, diethylene glycol, dipropylene glycol, triethylene glycol, tripropylene glycol, 1,3-butanediol, 1,4-butanediol, 1,5-pentanediol, 2-methyl-2,4-pentanediol, 3-methyl-1,5-pentanediol, 1,6-hexanediol, 2-ethyl-1,3-hexanediol, glycerol and diglycerol, monoalkyl or alkenyl (1 to 6 carbon atoms) ethers of these polyhydric alcohols, monoalkyl or alkenyl (1 to 6 carbonatoms) ether acetates of these polyhydric alcohols, diacetates of these polyhydric alcohols and dialkyl or alkenyl (1 to 6 carbon atoms) ethers of these polyhydric alcohols; high molecular weight polyvalent alcohols such as liquid (at ambient temperature) polyethylene glycols, liquid (at ambient temperature) polypropylene glycols and polyvinyl alcohols and mono or diethers of these polyhydric alcohols. Among these compounds (3), polyalkylene glycol monoalkyl ethers and polyalkylene glycol dialkyl ethers are preferable and diethylene glycol monoalkyl (1 to 6 carbon atoms) ethers, diethylene glycol dialkyl (1 to 6 carbon atoms) ethers, triethylene glycol monoalkyl (1 to 6 carbon atoms) ethers and triethylene glycol dialkyl (1 to 6 carbon atoms) ethers are more preferable.
4) Mono-, di- or tri-esters of an organic acid having 2 to 18 carbon atoms with a monohydric alcohol having 1 to 11 carbon atoms. Examples of the organic acid include acetic acid, propionic acid, butyric acid, stearic acid, oleic acid, lactic acid, benzoic acid, abietic acid, oxalic acid, malonic acid, phthalic acid, malic acid, succinic acid, maleic acid, fumaric acid, trimellitic acid, citric acid, etc. Examples of the monohydric alcohol having 1 to 11 carbon atoms are the same as those described in the above 2). Preferable examples among these examples are alkyl phthalates and alkyl trimellitates.
5) Plant oils such as soybean oil and cotton seed oil The agricultural chemical composition of the present invention comprises the agricultural chemical enhancer of the present invention which enhancer contains at least one of the compounds represented by the formulae (I) to (III) and a technical material of agricultural chemical. Here, the technical material of agricultural chemical means an effective component of an agricultural chemical. In the agricultural chemical composition of the present invention, the ratio by weight of the compounds represented by the formulae (I), (II) and (III) to the technical material of agricultural chemical is as follows: (compounds represented by the formulae (I) to (III))/(technical material of agricultural chemical)=preferably 0.001 to 100, more preferably 0.05 to 50 and particularly preferably 0.01 to 20. If the ratio falls in the above range, the good potency enhancing effect of the agricultural chemical is obtained.

Also, there is no limitation to the formulation form of the agricultural chemical composition of the present invention and the composition may have any formulation form including an emulsifiable concentrate, wettable powder, granule, dust formulation, suspension concentrate (flowable), etc. The agricultural chemical composition may therefore contain other additives, for example an emulsion, dispersant and carrier, etc., corresponding to its formulation form.

A chelating agent, pH regulator, inorganic salt and thickener may be added to the agricultural chemical composition of the present invention according to the need.

As the chelating agent, the same compounds that are used in the agricultural chemical enhancer may be used.

Examples of the pH regulator which may be used in the present invention include citric acid, phosphoric acid (pyrophosphoric acid), gluconic acid, etc. or salts of these acids.

Examples of the inorganic salts which may be used in the present invention include inorganic mineral salts such as inorganic salt clay, talc, bentonite, zeolite, calcium carbonate, diatomaceous earth and white carbon and inorganic ammonium salts such as ammonium sulfate, ammonium nitrate, ammonium phosphate, ammonium thiocyanate, ammonium chloride and ammonium sulfamate.

As the thickener which may be used in the present invention, any one of natural, semi-synthetic or synthetic water-soluble thickeners may be used. Specific examples of these thickeners include xanthane gum and zanflow derived from microorganisms, pectin, gum arabic, guar gum and the like derived from plants as the natural viscous materials; methylated products of cellulose or starch derivatives, carboxyalkylated products, hydroxyalkylated products, including methyl cellulose, carboxymethyl cellulose, hydroxymethyl cellulose etc., and sorbitol as the semi-synthetic viscous materials; and polyacrylates, polymaleates, polyvinyl pyrrolidone and pentaerythritol ethylene oxide adducts as the synthetic viscous materials.

Examples of the technical material of agricultural chemical used in the agricultural chemical composition of the present invention include compounds described in "AGRICULTURAL CHEMICAL HANDBOOK, 1998 edition" (10th edition, Dec. 15, 1998, published by (Corporation) Japan Plant Protection Association). Specific examples of these compounds are described below; however the present invention is not limited to these examples.

Examples of the fungicide (or bactericides) include organic sulfur fungicides (or bactericides) such as a zineb agent, maneb agent, thiram agent, mancozeb agent, polycarbamate agent and propineb agent, benzimidazole type fungicides (or bactericides) such as benomyl agent and thiophanate methyl agent, dicarboxylic acid type fungicides (or bactericides) such as an iprodione agent and procymidone agent, other synthetic fungicides (or bactericides) such as a triazine agent, iminoctadine acetate agent, isoprothiolane agent, TPN agent, probenazole agent, captan agent, fluorimide agent, DPC agent and iminocutadino albecilacetic acid, sterol biosynthetic inhibitors such as a triflumizole agent, bitertanol agent, pyrifenox agent, fenarimol agent, triforine agent, triadimefon agent, miclobutanil agent, defenoconazole agent and imibenconazole agent, acid amide type fungicides such as a metalaxyl agent and mepronil agent, copper fungicides such as inorganic copper agents and organic copper agents, antibiotic fungicides such as a streptomycin agent, polyoxin agent, blastcidin S agent, kasugamycin agent, validamycin and oxytetracycline agent, soil fungicides such as an echlomezol agent, hydroxyisoxazole agent, melamine biosynthetic inhibitors such as a fthalide agent and carpropamid agent, organic phosphorous type fungicides such as an IBP agent, EDDP agent and fosetyl agent, inorganic fungicides such as inorganic sulfur agents and hydrogen carbonate agents, methoxyacrylate type fungicides such as azoxystrobin and kresoxim methyl agent, anilinopyrimidine type fungicides such as mepanipyrim, synthetic fungicides such as oxolinic acid agents, natural product fungicides such as soybean recithin and fungicides derived from organisms such as anti-antibacterial agents.

Given as examples of the insecticide are a pyrethroid type insecticide such as a fenvalerate agent, cyfluthrin agent, pelmethrin agent, flucythrinate and ethofenprox agent, organic phosphorous type fungicides such as a DDVP agent, MEP agent, malathion agent, dimethoate agent, PAP agent, MPP agent, DMTP agent and EPN agent, carbamate type insecticide such as a BPMC agent, NAC agent and methomyl agent, neristochicine insecticides such as a cartap agent, natural product type insecticides such as pyrethrin agent derived from a pyrethrum, piperonylbutoxide agent, rotenone agent derived derris of a shrub of Leguminosae, nicotinic agent, soybean recithin and starch. Examples of the insect growth regulator include a diflubenzron agent, teflubenzuron agent, chlorofluzuron agent, buprofezin agent, isoprothiolane agent and flufenoxuron agent.

Examples of the miticides include a quercene agent, BPPS agent, fenbutatin oxide agent, hexathiazox agent, amitraz agent, fenproximate agent, tebufenpyrad agent, halfenprox agent and bialaphos agent. Examples of the chloronicotinyl type insecticide include imidacloprid agent etc. Examples of the other synthetic insecticides include a sodium oleate agent and liquid potassium oleate agent etc. Examples of the nematicide include a D-D agent, dazomet agent and benomyl agent, etc. Examples of insecticides derived from organisms include BT agents, etc.

Examples of the herbicide include acid amide type herbicides such as a DCPA agent, arachlor agent, asulam agent, etc., urea type herbicides such as a DCMU agent, linuron etc., bipyridinium type herbicides such as paraquate agent and diquat agent, diazine type herbicides such as a bromacil agent and renacil agent, S-triazine type herbicides such as a CAT agent and simetryn agent, other organic herbicides such as nitrile type herbicides, e.g., a DBN agent, sethoxydim agent, clethodim agent, etc., dinitroaniline type herbicides such as a trifluralin agent and pendimethalin agent, carbamate type herbicides such as thiobencarb agent, aromatic carboxylic acid type herbicides such as an MDBA agent, phenoxy acid type herbicides such as a 2,4-PA agent and a sihalofop-butyl agent, organic phosphorous type herbicides such as piperophos agent and butamifos agent, amino acid type herbicides such as a glyphosate agent, bialaphos agent and glufosinate agent, fatty acid type herbicides such as a pelargonic acid agent and DPA agent, sulfonylurea type herbicides such as thifensulfolonmethyl agent, flazasulfuron agent and bensulfuron-methyl agent, pyrimidyloxybenzoic acid type herbicides such as a bispyribac sodium salt agent and diazole type herbicides such as pyrazolynate.

Among these herbicides, acid amide type herbicides, diazine type herbicides, nitrile type herbicides, dinitroaniline type herbicides, aromatic carboxylic acid type herbicides and amino acid type herbicides are preferable and particularly a bialaphos agent and glufosinate agent or glyphosate agent among amino acid type herbicides are preferable.

Further, examples of the plant growth regulator include auxin antagonism agents such as a maleic hydrazide agent and uniconazole agent, auxin agents such as indolebutyric acid agent, 1-naphthaleneacetamide agent and 4-CPA agent, cytokinin agents such as forchlorfenuron agents, gibberellic acid agents such as a gibberellic acid agent, other growth retardants such as a daminozide agent, transpiration regulater such as paraffin agent, other plant growth regulator such as a choline agent, plant growth regulators derived from organisms such as a chlorella extract agent and ethylene agents such as ethephon.

Further, in the agricultural chemical composition, one or more of plant growth regulators, fertilizers, antiseptics and the like may be used by mixing these materials.

More specific examples of the formulation form of the agricultural chemical composition of the present invention include:

(a) agricultural chemical formulations comprising an encapsulated packaging body containing one or more of the compounds represented by the aforementioned formulae (I) to (III) and an encapsulated packaging body containing a technical material of agricultural chemical;

(b) agricultural chemical formulations comprising an encapsulated packaging body containing a mixture of one or more of the compounds represented by the aforementioned formulae (I) to (III) and one or more surfactants other than these compounds and an encapsulated packaging body containing a technical material of agricultural chemical;

(c) agricultural chemical formulations comprising an encapsulated packaging body containing one or more of the compounds represented by the aforementioned formulae (I) to (III), an encapsulated packaging body containing one or more surfactants other than these compounds and an encapsulated packaging body containing a technical material of agricultural chemical;

(d) agricultural chemical formulations comprising an encapsulated packaging body containing a mixture of one or more of the compounds represented by the aforementioned formulae (I) to (III) and a chelating agent and an encapsulated packaging body containing a technical material of agricultural chemical;

(e) agricultural chemical formulations comprising an encapsulated packaging body containing a mixture of one or more of the compounds represented by the aforementioned formulae (I) to (III) and achelating agent, an encapsulated packaging body containing one or more surfactants other than these compounds and an encapsulated packaging body containing a technical material of agricultural chemical; and (f) agricultural chemical formulations comprising an encapsulated packaging body containing a mixture of one or more of the compounds represented by the aforementioned formulae (I) to (III), one or more surfactants other than these compounds and a chelating agent and an encapsulated packaging body containing a technical material of agricultural chemical.

The structure in each of the encapsulated packaging bodies is adjusted corresponding to its use and object without any limitation.

The agricultural chemical enhancer of the present invention is compounded in commonly used plant or animal agricultural chemicals for use as agricultural chemical compositions or used together with the aforementioned agricultural chemicals, whereby the Preventive effect of the agricultural chemicals can be significantly improved. Also, the agricultural chemical enhancer of the present invention has high safety. As mentioned above, the use of the agricultural chemical enhancer of the present invention makes it possible to improve the activity of conventional agricultural chemicals and to promote the growth of plant bodies to be intended to be grown. Therefore, the agricultural chemicals enhancer of the present invention is very significant for producers.

EXAMPLES

Example 1

(A) The compounds represented by the formulae (I) to (III), (B) surfactants and (C) chelating agents were used as shown in Table 1 to produce various agricultural chemical enhancers.

Each of these agricultural chemical enhancers was dissolved in ion exchange water in a concentration of 0.02% by weight. Using the resulting 0.02 wt % diluted solution, a Roundup liquid agent (containing 41% by weight of an effective component as a glyphosate isopropylamine salt) which was a commercially available herbicide and an aqueous Herbiace solvent (containing 20% by weight of an effective component as bialaphos) were respectively diluted at a dilution of 1:300, to obtain two agricultural chemical compositions on one effective component.

Crabgrass seeds were planted in a pot having an inside diameter of 12 cm and filled with a fertile soil sampled from a paddy field for a test in a greenhouse, river sand and commercially available culture soil in a ratio of 7:2:1 (weight ratio) to germinate. In order to increase the uniformity of individuals among these pots, pots in which abnormal growth was observed were wasted. Pots in which crabgrass was grown to a height of about 18 cm were used for the test. The agricultural chemical composition was sprayed using a spray gun (RG type, manufactured by Iwata Air Compressor Mfg. Co., Ltd.) such that it was sprayed uniformly over the whole of digitaria in the pot in a proportion corresponding to 10 liters/are to evaluate the herbicidal effect.

In the evaluation of the herbicidal-effect, product weight on the ground was weighed 10th day after the spraying treatment to show a herbicidal ratio based on the product weight on the ground in an untreated division (see the following equation). The herbicidal ratio of each agricultural chemical composition is shown in Table 2.

$$\text{Herbicidal ratio (\%)} = \frac{\text{Product weight on the ground in an untreated division }(g) - \text{Product weight on the ground in a treated division }(g))}{\text{Product weight on the ground in an untreated division }(g)} \times 100$$

Example 2

25 female mites (Tetranychus kanzawai Kishida) per division were implanted on a leaf disk of a green bean by a 4-times-recurrent backcross method and then incubated at 25° C. for 24 hours. As the leaf disk, a circular one having a diameter of 4 cm was used. After that, the whole of the leaf disk was dipped in a test solution for 5 seconds and then taken out of the test solution and allowed to stand at 25° C. for 48 hours. Then, the condition of the mites was observed to find miticidal ratio based on the case of the untreated division (see the equation shown below). As the miticide, an Osadan wettable powder 25 (containing 25% by weight of an effective component as fenbutatin oxide) diluted at a dilution of 1:2000 was used and the same one that was used in Example 1 was used as the agricultural chemical enhancer. The agricultural chemical enhancer was used such that the concentration of the effective component thereof in the diluted solution was adjusted to 0.1% by weight. Also, the same test was carried out in the case of using no agricultural chemical enhancer. The miticidal ratio was found by the following equation. Also, at the same time, the SPAD value indicating the grade of greenness of a leaf of the leaf disk was measured using a "Minolta Chlorophyll Measuring Meter SPAD 502" (manufactured by Minolta Camera Co. Ltd.). SPAD values at 30 points per division were measured and an average of these measured values was found. The average value was expressed as a relative value when the SPAD value in the untreated division was set to 100. The results are shown in Table 3.

$$\text{Miticidal ratio (\%)} = \frac{\text{the number of survival mites in an untreated division} - \text{the number of survival mites in a treated division}}{\text{the number of survival mites in an untreated division}} \times 100$$

Example 3

The whole of a leaf disk of a green bean was dipped in a test solution for 5 seconds, taken out of the test solution and dried in air. Then, 10 rice planthopper larvae of third instar which had been incubated in advance were put on a leaf disk and incubated at 25° C. for 10 days. The number of dead rice planthopper was observed by the naked eye to certificate the potency of the insecticide. As the leaf disk, a circular one having a diameter of 4 cm was used. The test was repeated ten times and the insecticidal ratio was calculated in the same manner as in the case of the miticidal ratio. As the insecticide, an Aproad wettable powder (containing 25% by weight of an effective component as buprofezin) diluted at a dilution of 1:2000 was used and the same one that was used in Example 1 was used as the agricultural chemical enhancer such that the concentration of the effective component thereof in the diluted solution was adjusted to 0.025% by weight. Also, at the same time, the SPAD value was measured in the same manner as in Example 2. The results are shown in Table 4.

Example 4

A suspension ($10^7$/ml) of the spores of Botrytis cinerea which was germicide-resistant bacteria was sprayed on the juvenile seedling (three main leaves were developed) of a cucumber in an amount of 10 ml per pot and allowed to stand under the condition of a temperature of 25° C. and a relative humidity of 90% for one day. The repetition of the pot per division was designed to be 10. Then, a commercially available Benlate wettable powder (containing 50% by weight of an effective component as benomyl) diluted at a dilution of 1:2000 with a 0.025% dilute solution of the agricultural chemical enhancer used in Example 1. Then, the diluted solution was sprayed in an amount of 5 ml per pot. After that, the sample was allowed to stand under the condition of a temperature of 25° C. and a relative humidity of 85%. The number of lesions was counted 14 days after the germicide was sprayed to find the preventive value as compared with that in an untreated division according to the following equation. Also, a height and a fresh weight (the total of fresh weights above and under the ground) were measured and expressed as relative values when each of these height and product weight in a division where the agricultural chemical was singly used was put to 100. The results are shown in Table 5.

$$\text{Preventive value} = 1 - \frac{\text{(Number of lesions in a treated division)}}{\text{Number of lesions in an untreated division}} \times 100$$

Examples 1 to 4 show the cases where the potency of the agricultural chemical enhancer of the present invention was compared with the case (comparative product) of using a usual surfactant as an agricultural chemical enhancer. As is clear from Tables 2 to 5, the agricultural chemical enhancer of the present invention produced its effect significantly and promoted the growth of a plant body to be intended to be grown.

Tables 1 to 5 are described below.

TABLE 1

| | | Compound name | (A)/(B)/(C) weight ratio |
|---|---|---|---|
| Product of the invention | 1 | (A) 1-hexadecanol<br>(B) POE(40)sorbitol tetraoleate<br>(C) — | 25/75/0 |
| | 2 | (A) Distearic acid ethylene glycol (Emanone 3201M, manufactured by Kao Co.)<br>(B) POE(20)lauryl ether<br>(C) Citric acid | 25/70/5 |
| | 3 | (A) 1-octadecanol<br>(B) POE(20)sorbitan monooleate<br>(C) EDTA·4Na | 20/70/10 |
| | 4 | (A) 1,2-Octadecanediol<br>(B) Sodium POE(3) lauryl ether sulfate<br>(C) — | 20/80/0 |
| | 5 | (A) 1-Tetracosanol<br>(B) POE(20) sorbitan monooleate<br>(C) Malic acid | 20/70/10 |
| | 6 | (A) Dioctadecyl ether<br>(B) POE(20) hardened castor oil<br>(C) Heptonic acid | 25/70/5 |
| | 7 | (A) Oleyl alcohol<br>(B) Laurylamidopropylbetaine<br>(C) — | 20/80/0 |
| | 8 | (A) 1-Octadecanediol<br>(B) POE(20) sorbitan monooleate<br>(C) — | 25/75/0 |
| | 9 | (A) $C_{18}H_{37}O(EO)_5C_{18}H_{37}$<br>(B) —<br>(C) — | 100/0/0 |
| | 10 | (A) 2-Octadecanol<br>(B) POE(13) cetyl ether<br>(C) — | 33/67/0 |
| | 11 | (A) 2-Eicosanol<br>(B) Na POE(4.5) lauryl ether acetate<br>(C) 3Na citrate | 20/75/5 |
| | 12 | (A) 15-hexadecene-1-ol<br>(B) POE(40) sorbit tetraoleate<br>(C) EDTA·2Na | 25/70/5 |
| | 13 | (A) $C_{18}H_{37}O(EO)_5C_{18}H_{37}$<br>(B) —<br>(C) EDTA·4Na | 70/0/30 |
| | 14 | (A) 1-Octadecanol<br>(B) POE(80) hardened castor oil<br>(C) 3Na citrate | 23/68/9 |
| | 15 | (A) 1-Octadecanol<br>(B) POE(40) hardened castor oil<br>(C) — | 25/75/0 |
| Comparative product | 16 | (A) —<br>(B) POE(20) sorbitan monooleate<br>(C) — | 0/100/0 |
| | 17 | (A) —<br>(B) Sodium POE(3) lauryl ether sulfate<br>(C) — | 0/100/0 |

TABLE 2

| Enhancer for agicultural chemical No. | Herbicidal ratio (%) | |
|---|---|---|
| | Roundup liquid agent | Herbiace wettabale powder |
| Product of the invention | | |
| 1 | 95.9 | 88.9 |
| 2 | 95.8 | 87.1 |
| 3 | 98.9 | 91.0 |
| 4 | 96.3 | 88.1 |
| 5 | 97.0 | 88.2 |
| 6 | 96.5 | 89.0 |

TABLE 2-continued

| Enhancer for agicultural chemical No. | Herbicidal ratio (%) Roundup liquid agent | Herbiace wettabale powder |
|---|---|---|
| 7 | 96.0 | 87.0 |
| 8 | 97.2 | 89.5 |
| 9 | 95.2 | 87.3 |
| 10 | 96.5 | 88.1 |
| 11 | 96.0 | 87.9 |
| 12 | 94.2 | 86.9 |
| 13 | 96.3 | 88.1 |
| 14 | 98.8 | 90.7 |
| 15 | 97.2 | 89.6 |
| Comparative product | | |
| 16 | 74.2 | 69.9 |
| 17 | 72.7 | 67.5 |
| Treatment only with an agricultural chemical | 70.3 | 65.4 |

TABLE 3

| Enhancer for agricultural chemical No. | Miticidal ratio (%) | SPAD value |
|---|---|---|
| Product of the invention | | |
| 1 | 95 | 114 |
| 2 | 93 | 112 |
| 3 | 98 | 120 |
| 4 | 95 | 116 |
| 5 | 94 | 114 |
| 6 | 94 | 116 |
| 7 | 95 | 113 |
| 8 | 96 | 117 |
| 9 | 94 | 113 |
| 10 | 95 | 115 |
| 11 | 93 | 112 |
| 12 | 94 | 112 |
| 13 | 95 | 114 |
| 14 | 98 | 119 |
| 15 | 96 | 117 |
| Comparative product | | |
| 16 | 61 | 102 |
| 17 | 60 | 101 |
| Treatment only with an agricultural chemical | 58 | 100 |

TABLE 4

| Enhancer for agricultural chemical No. | Insecticidal ratio (%) | SPAD value |
|---|---|---|
| Product of the invention | | |
| 1 | 94 | 115 |
| 2 | 92 | 113 |
| 3 | 97 | 121 |
| 4 | 94 | 115 |
| 5 | 94 | 114 |
| 6 | 94 | 115 |
| 7 | 92 | 111 |
| 8 | 96 | 117 |

TABLE 4-continued

| Enhancer for agricultural chemical No. | Insecticidal ratio (%) | SPAD value |
|---|---|---|
| 9 | 93 | 114 |
| 10 | 90 | 113 |
| 11 | 89 | 110 |
| 12 | 88 | 113 |
| 13 | 94 | 116 |
| 14 | 96 | 120 |
| 15 | 95 | 116 |
| Comparative product | | |
| 16 | 60 | 102 |
| 17 | 58 | 101 |
| Treatment only with an agricultural chemical | 55 | 100 |

TABLE 5

| Enhancer for agricultural chemical No. | Preventive value | Height | Fresh weight |
|---|---|---|---|
| Product of the invention | | | |
| 1 | 87 | 108 | 119 |
| 2 | 86 | 107 | 119 |
| 3 | 92 | 117 | 128 |
| 4 | 87 | 110 | 119 |
| 5 | 87 | 109 | 120 |
| 6 | 89 | 112 | 121 |
| 7 | 88 | 111 | 120 |
| 8 | 90 | 113 | 125 |
| 9 | 87 | 109 | 116 |
| 10 | 88 | 110 | 119 |
| 11 | 86 | 108 | 114 |
| 12 | 84 | 110 | 111 |
| 13 | 89 | 110 | 118 |
| 14 | 91 | 116 | 128 |
| 15 | 89 | 113 | 124 |
| Comparative product | | | |
| 16 | 70 | 102 | 102 |
| 17 | 68 | 100 | 101 |
| Treatment only with an agricultural chemical | 58 | 100 | 100 |

The invention claimed is:

1. An agricultural chemical enhancer composition, comprising at least one compound selected from the group consisting of a compound represented by the formula (I), a compound represented by the formula (II) and a compound represented by the formula (III) as an effective component, and at least one compound selected from the group consisting of a surfactant that is other than the said compound represented by the formula (I), (II) or (III), and a chelating agent:

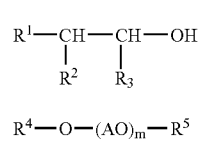

-continued

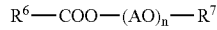 (III)

wherein $R^1$ represents a hydrocarbon group having 10 to 22 carbon atoms, $R^2$ represents a hydroxyl group, $R^3$ represents a hydrogen atom or a hydrocarbon group having 1 to 24 carbon atoms, $R^4$ represents a hydrocarbon group having 12 to 24 carbon atoms, $R^5$ represents a hydrocarbon group having 1 to 24 carbon atoms, AO represents an alkylene oxide group having 2 to 4 carbon atoms, m denotes a number of 0 to 50, n denotes a number of 0 to 50, $R^6$ represents a hydrocarbon group having 11 to 23 carbon atoms, $R^7$ represents a hydrocarbon group having 12 to 24 carbon atoms or —$COR^8$, where $R^8$ represents a hydrocarbon group having 11 to 23 carbon atoms, and provided that n is 1 when $R^7$ is —$COR^8$.

2. The agricultural chemical enhancer composition according to claim 1, wherein the surfactant is at least one surfactant selected from the group consisting of (1) a nonionic surfactant having at least one of an ester bond, an ether bond and an amide bond, (2) an anionic surfactant, (3) a cationic surfactant and (4) an amphoteric surfactant.

3. The agricultural chemical enhancer composition according to claim 1, wherein the surfactant is (1) a nonionic surfactant having at least one of an ester bond and an ether bond.

4. The agricultural chemical enhancer composition according to claim 1, 2 or 3, further comprising a technical material of an agricultural chemical.

5. A method for enhancing the potency of an agricultural chemical and improving the growth of a plant by applying an agricultural chemical enhancer composition to a plant together with an agricultural chemical;

wherein the agricultural chemical enhancer composition comprises at least one compound selected from the group consisting of a compound represented by the formula (I), a compound represented by the formula (II) and a compound represented by the formula (III) as an effective component:

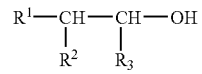 (I)

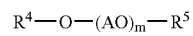 (II)

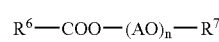 (III)

wherein $R^1$ represents a hydrocarbon group having 10 to 22 carbon atoms, $R^2$ represents a hydroxyl group, $R^3$ represents a hydrogen atom or a hydrocarbon group having 1 to 24 carbon atoms, $R^4$ represents a hydrocarbon group having 12 to 24 carbon atoms, $R^5$ represents a hydrocarbon group having 1 to 24 carbon atoms, AO represents an alkylene oxide group having 2 to 4 carbon atoms, m denotes a number of 0 to 50, n denotes a number of 0 to 50, $R^6$ represents a hydrocarbon group having 11 to 23 carbon atoms, $R^7$ represents a hydrocarbon group having 12 to 24 carbon atoms or —$COR^8$, where $R^8$ represents a hydrocarbon group having 11 to 23 carbon atoms, and provided that n is 1 when $R^7$ is —$COR^8$.

6. The method for enhancing the potency of an agricultural chemical and improving the growth of a plant as claimed in claim 5, wherein said agricultural chemical enhancer composition further comprises at least one compound selected from the group consisting of a surfactant that is other than the said compound represented by the formula (I), (II) or (III), and a chelating agent.

7. The method for enhancing the potency of an agricultural chemical and improving the growth of a plant as claimed in claim 6, wherein the surfactant is at least one surfactant selected from the group consisting of (1) a nonionic surfactant having at least one of an ester bond, an ether bond and an amide bond, (2) an anionic surfactant, (3) a cationic surfactant and (4) an amphoteric surfactant.

8. The method for enhancing the potency of an agricultural chemical and improving the growth of a plant as claimed in claim 6, wherein the surfactant is (1) a nonionic surfactant having at least one of an ester bond and an ether bond.

* * * * *